United States Patent [19]

Carter

[11] Patent Number: 5,298,221
[45] Date of Patent: Mar. 29, 1994

[54] INHIBITION OF SCALE FORMATION AND CORROSION BY SULFONATED ORGANOPHOSPHONATES

[75] Inventor: Charles Garvie Carter, Silver Spring, Md.

[73] Assignee: W. R. Grace & Co. - Conn., New York, N.Y.

[21] Appl. No.: 32,457

[22] Filed: Mar. 17, 1993

Related U.S. Application Data

[62] Division of Ser. No. 782,843, Oct. 24, 1991, Pat. No. 5,221,487.

[51] Int. Cl.$^5$ ............................................. C23F 11/167
[52] U.S. Cl. .............................. 422/15; 252/389.22; 252/389.23; 210/699
[58] Field of Search ............ 210/699, 700; 252/180, 252/389.21, 389.22, 389.23; 422/15

[56] References Cited

U.S. PATENT DOCUMENTS

| | | | |
|---|---|---|---|
| 3,617,576 | 11/1971 | Kerst | 210/699 |
| 3,705,191 | 12/1972 | Kerst | 260/502.4 P |
| 3,714,066 | 1/1973 | King et al. | 252/181 |
| 3,733,270 | 5/1973 | Kerst | 210/699 |
| 3,833,690 | 9/1974 | Kerst | 260/932 |
| 3,855,284 | 12/1974 | Germscheid | 260/502.4 A |
| 3,957,160 | 5/1976 | Ploger | 210/700 |
| 3,957,858 | 5/1976 | Kerst | 210/699 |
| 4,085,134 | 4/1978 | Redmore et al. | 252/180 |
| 4,172,787 | 10/1979 | Ries et al. | 252/180 |
| 4,212,734 | 7/1990 | Redmore et al. | 252/180 |
| 4,216,163 | 8/1980 | Sommer et al. | 252/180 |
| 4,229,294 | 10/1980 | Redmore et al. | 210/700 |
| 4,239,695 | 12/1980 | Chai et al. | 210/700 |
| 4,250,107 | 2/1981 | Sommer et al. | 210/700 |
| 4,640,818 | 2/1987 | Grierson | 722/15 |
| 4,756,881 | 7/1988 | Hoots et al. | 422/13 |
| 4,798,675 | 1/1989 | Lipinski et al. | 210/700 |
| 4,810,486 | 3/1989 | Kelly et al. | 534/14 |
| 5,043,099 | 8/1991 | Kreh et al. | 562/13 |

FOREIGN PATENT DOCUMENTS 2625767 12/1977 Fed. Rep. of Germany.

*Primary Examiner*—Peter A. Hruskoci
*Attorney, Agent, or Firm*—James P. Barr

[57] ABSTRACT

A method is disclosed for inhibiting or preventing the formation of scale and corrosion on surfaces in contact with an aqueous system comprising adding to the system an amount effective to inhibit scale formation of a sulfonated organophosphonate compound having the formula:

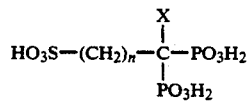

wherein n is an integer from 3 to 10, X is OH or $NH_2$; and water soluble salts thereof.

12 Claims, No Drawings

INHIBITION OF SCALE FORMATION AND CORROSION BY SULFONATED ORGANOPHOSPHONATES

This is a division of application Ser. No. 07/782,843, filed Oct. 24, 1991 now U.S. Pat. No. 5,221,487.

FIELD OF THE INVENTION

This invention relates to a method for inhibiting or preventing the formation of scale on surfaces which are in contact with an aqueous system and for inhibiting the corrosion of ferrous-based metals which are in contact with an aqueous system. More specifically, it relates to a method wherein a sulfonated organophosphonate is added to an aqueous system in an amount effective to inhibit the formation of scale and/or to inhibit the corrosion of a ferrous-based metal.

BACKGROUND OF THE INVENTION

Most industrial aqueous systems contain alkaline earth metal cations, such as calcium, magnesium, and the like, as well as numerous anions such as bicarbonate, carbonate, sulfate, and the like. When the concentration of the various combinations of cation and anions exceed the solubility of their reaction products, precipitates tend to form until the product solubility concentrations are no longer exceeded. As these reaction products precipitate on the surfaces of the aqueous systems, they form what is known as scale. The precipitation of calcium carbonate is by far the most common form of scale in industrial aqueous systems. This occurs when the ionic product of calcium and carbonate exceeds the solubility of the calcium carbonate and a solid phase of calcium carbonate forms.

The formation of scale in industrial aqueous systems represents a major problem since it reduces heat transfer efficiency on heat exchanger surfaces, increases corrosion problems and reduces flow of the water through the system. The addition of inorganic and, more recently, all organic polyphosphonates to these aqueous systems is known to inhibit scale formation. These compositions are generally added to the system in sub-stoichiometric amounts to the scale forming salt and are known to those in the art as threshold inhibitors. Threshold inhibition describes the phenomenon whereby a sub-stoichiometric amount of a scale inhibitor can stabilize a solution from precipitation. Threshold inhibition generally takes place under conditions where a small amount, e.g. 1 ppm to 100 ppm of a polymeric inhibitor, will stabilize the solution which contains many orders of magnitude greater concentration of scale forming salts.

Iron and iron-based metal-containing alloys, such as mild steel, are well-known materials used in constructing the apparatus of aqueous systems. In these systems water circulates, contacts the ferrous-based metal surface, and may be concentrated, such as by evaporation of a portion of the water from the system. Even though such metals are readily subject to corrosion in such environments, they are used over other metals due to their strength and availability.

It is known that various materials which are naturally or synthetically occurring in the aqueous systems, especially systems using water derived from natural resources such as seawater, rivers, lake and the like, attack ferrous-based metals. The term "ferrous-based metals", as used herein, refers to any ferrous-containing metals. Typical devices in which the ferrous-based metal parts are subject to corrosion include evaporators, single and multi-pass heat exchangers, cooling towers, and associated equipment and the like. As the system water passes through or over the device, a portion of the system water evaporates causing a concentration of the dissolved materials contained in the system. These materials approach and reach a concentration at which they may cause severe pitting and corrosion which eventually requires replacement of the metal parts. Various corrosion inhibitors have been previously used.

Chromates and inorganic phosphates or polyphosphates have been used in the past to inhibit the corrosion of metals which is experienced when the metals are brought into contact with water. The chromates, though effective, are highly toxic and, consequently, present handling and disposal problems. Phosphates are non-toxic. However, due to the limited solubility of calcium phosphate, it is difficult to maintain adequate concentrations of phosphates in many instances. The polyphosphates are also relatively non-toxic, but tend to hydrolyze to form orthophosphate which in turn, like phosphate itself, can create scale and sludge problems in aqueous systems (e.g. by combining with calcium in the system to form calcium phosphate). Moreover, where there is concern over eutrophication of receiving waters, excess phosphate compounds can provide disposal problems as nutrient sources. Borates, nitrates and nitrites have also been used for corrosion inhibition. These too, can serve as nutrients in low concentrations, and/or represent potential health concerns at high concentrations.

In addition, environmental considerations have also recently increased concerns over the discharge of other metals, such as zinc, which previously were considered acceptable for water treatment.

Much recent research has been concerned with the development of organic scale and corrosion inhibitors which can reduce reliance on the traditional inorganic inhibitors. Among the organic inhibitors successfully employed are numerous organic phosphonates. These compounds may generally be used without detrimentally interfering with other conventional water treatment additives. There is a continuing need, however, for safe and effective water treatment agents which can be used to control corrosion.

Many of the organic scale inhibitors and corrosion inhibitors used in industrial aqueous systems (e.g. hydroxyethylidine diphosphonic acid) are themselves very sensitive to calcium hardness and prone to form deposits of their calcium salts. This limits the range of hardness in which such materials can be usefully applied as scale inhibitors or corrosion inhibitors. There is a continuing need for safe and effective water treating agents which can be used to control scale formation and to exhibit corrosion, particularly when substantial calcium carbonate is present in the system water.

SUMMARY OF THE INVENTION

It is an object of this invention to provide a method of inhibiting or preventing the formation of scale in aqueous systems.

It is another object of this invention to provide a method of inhibiting corrosion of ferrous-based metals which are in contact with aqueous systems.

In accordance with the present invention, there has been provided a method of inhibiting scale formation on surfaces in contact with an aqueous system wherein a sulfonated organophosphonate compound having the formula:

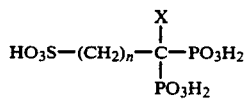

wherein n is an integer from 3 to 10; X is OH or $NH_2$; and water soluble salts thereof are added to the aqueous system in an amount effective to inhibit scale formation.

Also in accordance with the present invention, there has been provided a method of inhibiting corrosion of ferrous based metals which are in contact with an aqueous system wherein a sulfonated organophosphonate compound having the formula:

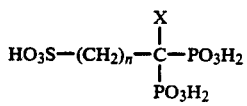

wherein n is an integer from 3 to 10; X is OH or $NH_2$; and water soluble salts thereof are added to the aqueous system in an amount effective to inhibit corrosion of ferrous-based metals.

DETAILED DESCRIPTION

The present invention is directed to a novel method of inhibiting the formation of scale in aqueous systems and of inhibiting corrosion of ferrous-based metals in contact with aqueous systems. The methods involve adding to the aqueous systems a sulfonated organophosphonate compound in an amount effective to inhibit scale formation and/or to inhibit corrosion. The acid form of the sulfonated organophosphonate compounds of this invention can be represented by the general formula:

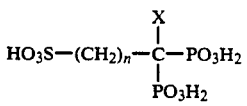

wherein n is an integer from 3 to 10; X is OH or $NH_2$.

The sulfonated organophosphonate compounds may also be used in the form of a water soluble salt such as an alkali metal salt and usually as the sodium salt. Other suitable water soluble salts include potassium, ammonium, zinc, lower amine salts, and the like. The free acids may also be used and all of the acidic hydrogens need not be replaced nor need the cation be the same for those replaced. Thus, the cation may be any one of or a mixture of $NH_4$, H, Na, K, etc. The sulfonated organophosphonates may be converted into the corresponding water soluble salts by conventional methods which are well known to those skilled in the art.

The sulfonated organophosphonate scale and corrosion inhibitors of this invention are particularly suitable for use in aqueous systems having a high degree of hardness and have exhibited a high degree of insensitivity to calcium. It is considered an important feature of this invention, that the claimed compositions be calcium insensitive. Calcium sensitivity refers to the tendency of a compound to precipitate with calcium ions in solution. The calcium insensitivity of the claimed compositions permits their use in aqueous systems having water with relatively high hardness. The test for calcium insensitivity of a compound, as used in this application, involves a cloud point test (hereinafter the CA500 cloud point test) where the compound is added to hard water containing 500 ppm calcium ion (as $CaCO_3$) which is buffered at pH 8.3 using 0.005M borate buffer and which has a temperature of 60° C. The amount of compound which can be added to the solution until it becomes turbid (the cloud point) is considered to be an indicator of calcium insensitivity.

The calcium insensitive compounds of this invention have cloud points of at least about 50 ppm as determined by the CA500 cloud point test, and preferably have cloud points of at least about 75 ppm, and most preferably have cloud points of at least 100 ppm as determined by the CA500 cloud point test.

The preparation of the sulfonated organophosphonate compounds of this invention can be carried out by two different methods. When the sulfonated organophosphonates of this invention are in the form of sulfonated aminodiphosphonates the preparation involves treating a sulfonated nitrile with phosphorous acid at an elevated temperature. This procedure is more fully described in U.S. Pat. No. 4,239,695 to B. J. Chai et al which is incorporated herein by reference in its entirety. When the sulfonated organophosphonates of this invention are in the form of sulfonated hydroxydiphosphonates, the preparation involves treating a halogenated carboxylic acid with $PCl_3$ and water to form a halogenated hydroxydiphosphonate. This procedure is more fully described in U.S. Pat. No. 3,855,284 to H. G. Germscheld which is incorporated herein by reference in its entirety. The halogenated hydroxydiphosphonate may be converted into the sulfonated hydroxydiphosphonates of the present invention by treatment with sodium sulfite under aqueous conditions according to the teaching of *Advanced Organic Chemistry*, 3rd Ed., J. March, pp 363–364, John Wiley & Sons, New York, NY (1985) which is incorporated here by reference.

The aqueous systems which may be advantageously treated with the sulfonated organophosphonate compounds of this invention include, but are not limited to cooling water systems such as e.g. cooling towers, desalinization units, gas scrubbers, as well as boiler systems and other recirculating water systems where scale deposits are known to form. The present invention is particularly useful in the treatment of cooling water systems which operate at temperatures between 60° F. and 200° F., particularly open recirculating cooling water systems which operate at temperatures of from about 80° F. to 150° F.

The precise dosage of the scale and/or corrosion inhibiting agents of this invention depends, to some extent, on the nature of the aqueous system in which it is to be incorporated and the degree of protection desired. In general, however, the concentration of sulfonated organophosphonates maintained in the system can be from about 0.05 to about 10,000 ppm. Within this range, generally low dosages of about 500 ppm or less are preferred, with a dosage of about 100 ppm or less being most preferred for many aqueous systems, such as for example, many open recirculating cooling water systems. Typically dosages of about 0.5 ppm or more are preferred, with a dosage of about 2 ppm or more being most preferred. The exact amount required with respect to a particular aqueous system can be readily determined by one of ordinary skill in the art in conventional manners. As is typical of most aqueous systems, the pH is preferably maintained at 6.5 or above, and is most preferably maintained at 7.5 or above.

The scale and/or corrosion inhibiting agents of this invention may be added to the system water by any convenient mode, such as by first forming a concentrated solution of the treating agent with water, preferably containing between 1 and 50 total weight percent of the sulfonated organophosphonate compound, and then feeding the concentrated solution to the system water at some convenient point in the system. In many instances the treatment agent may be added to the make-up water or feed water lines through which water enters the system. For example, an injection calibrated to deliver a predetermined amount periodically or continuously to the make-up water may be employed.

It will be appreciated that while the compositions of this invention may be used as the sole scale and/or corrosion inhibitor for the aqueous system, other conventional water treatment compositions customarily employed in aqueous systems may advantageously be used in combination with the claimed treatment agents. Thus, other suitable water treatment additives which may be used in combination with the sulfonated organophosphonates of this invention which include, but are not limited to, biocides, other scale inhibitors, chelants, sequestering agents, dispersing agents, corrosion inhibitors, polymeric agents (e.g. copolymers of 2-acrylamido-2-methyl propane sulfonic acid and methacrylic acid or polymers of acrylic acid and methacrylic acid), and the like.

Without further elaboration, it is believed that one of skill in the art, using the preceding detailed description, can utilize the present invention to its fullest extent.

The following examples are provided to illustrate the invention in accordance with the principles of this invention, but are not to be construed as limiting the invention in any way except as indicated in the appended claims. All parts and percentages are by weight unless otherwise indicated.

EXAMPLE 1

Potassium cyanide (3.5 g, 50 mmol) was dissolved in 100 ml methanol under an atmosphere of nitrogen. A solution of propane sulfone (6.1 g, 50 mmol) in 10 ml methanol was added and the mixture was heated to reflux for one hour. After cooling, the methanol was removed by distillation at reduced pressure leaving a white solid. The identity of the product as the potassium salt of 3-cyanopropanesulfonic acid was confirmed by proton nuclear magnetic resonance (NMR) spectroscopy.

EXAMPLE 2

A mixture of phosphorous acid (3.3 g, 40 mmol) and the sodium salt of 3-cyanopropanesulfonic acid (1.9 g, 10 mmol) was heated with a 175° C. oil bath for 16 hours. During this period, the reactants initially formed a melt and then gradually transformed to a yellow gum. After cooling and the addition of 50 ml of methanol, the resulting slurry was allowed to stir at room temperature overnight. After filtration, 2.2 g of a white powder was obtained. Characterization by proton, phosphorus and carbon NMR showed the product to be an impure sample of the potassium salt of 4-sulfo-1-aminobutane-1,1-diphosphonic acid.

EXAMPLE 3

The potassium salt of 3-cyanopropanesulfonic acid (1.9 g, 10 mmol) was added to a melt of phosphorous acid (3.3 g, 50 mmol). After the temperature of the oil bath used to heat the mixture was raised to 190° C., phosphorous trichloride (0.9 g, 5.8 mmol) was added. Heating was continued for 2 hours. The mixture was then cooled and 50 ml of water was added. The solution was then refluxed overnight. After cooling, the solution was diluted with 5 parts by volume of methanol and the resulting solid (0.16 g) collected by filtration. The mother liquor was concentrated, redissolved in 15 ml water and diluted with 45 ml methanol. After filtration, an additional 0.7 g of a solid was collected. The identity of the solid as the potassium salt of 4-sulfo-1-aminobutane-1,1-diphosphonic acid was confirmed by FAB mass spectroscopy and by proton, phosphorus and carbon NMR.

EXAMPLE 4

Sodium 7-cyanoheptanesulfonate (8.75 g, 41 mmol) was added to a melt of phosphorous acid (13.45 g, 164 mmol). After the temperature of the oil bath used to heat the reaction mixture reached 190° C., phosphorus trichloride (0.8 g, 6 mmol) was added as a catalyst. Heating was continued for 5 hours.

The reaction mixture was then cooled and 150 ml methanol was added. The mixture was heated for 1 hour, then cooled and filtered with suction. After drying in a vacuum oven to remove residual methanol, 3.1 g of a cream-colored powder was obtained. The identity of the solid as the monosodium salt of 7-sulfo-1-aminoheptane-1,1-diphosphonic Acid was confirmed by proton, carbon, and phosphorus NMR.

EXAMPLE 5

5-Bromovaleric acid (2.5 g, 14 mmol) and water (0.6 g, 35 mmol) were heated to 40° C. to form a melt. Phosphorus trichloride (3.2 g, 23 mmol) was added dropwise and the resulting mixture was heated to reflux for three hours. After cooling to room temperature, a solution of potassium hydroxide (1.3 g, 23 mmol) and sodium sulfite (1.8 g, 14 mmol) in water (15 ml) was added cautiously. The reaction mixture was heated to reflux for 19 hours, then cooled. Analysis of the product by phosphorus, proton and carbon NMR showed it to be 5-sulfo-1-hydroxypentane-1,1-diphosphonic acid containing small amounts of ortho-phosphate and 1,5-dihydroxypentane-1,1-diphosphonic acid.

EXAMPLE 6

A mixture of 8-bromooctanoic acid (7.0 g, 30 mmol) and water (1.3 g) were heated to about 40° C. to form a melt. The reaction was protected by a drying tube and phosphorus trichloride (6.9 g, 50 mmol) was added dropwise. The reaction mixture was then heated with an 150° C. oil bath for four to five hours. After cooling to room temperature, an aqueous solution of potassium hydroxide (2.8 g, 50 mmol) was added. The resulting mixture was then stirred overnight at room temperature. Sodium sulfite (3.8 g, 30 mmol) was added and the solution was heated to reflux for six hours, allowed to stand at room temperature overnight and finally refluxed for an additional seven hours. After cooling and dilution with water, the solution was treated with activated charcoal and filtered. Examination of the product by proton, phosphorus and carbon NMR showed it to be the desired 8-sulfo-1-hydroxyoctane-1,1-diphosphonic acid containing small amounts of ortho-phosphate and 1,8-dihydroxyoctane-1,2-diphosphonic acid.

EXAMPLE 7

1-Bromohexanoic acid (5.8 g, 30 mmol) and water (1.4 g, 75 mmol) were mixed and heated to 40° C. to form a melt. Phosphorus trichloride (6.9 g, 50 mmol) was added dropwise. The reaction mixture was heated to reflux for three hours, then cooled to room temperature. A solution of potassium hydroxide (2.8 g, 50 mmol) and sodium sulfite (3.8 g, 30 mmol) in 30 ml of water was added cautiously. The resulting mixture was heated to reflux for 18 hours, then cooled. Analysis of the product by proton, phosphorus and carbon NMR showed it to be the desired 6-sulfo-1-hydroxyhexane-1,1-diphosphonic acid containing small amounts of ortho-phosphate and 1,6-dihydroxyhexane-1,1-diphosphonic acid.

EXAMPLE 8

The calcium carbonate threshold inhibitor shaker test measures the ability of a chemical to inhibit calcium carbonate scale formation. The laboratory tests were performed under the following water conditions: water containing 1200 ppm $HCO_3^-$ and 1000 ppm $Ca^{+2}$ (both as $CaCo_3$). A solution of 75 ml of $NaHCO_3$ solution (2400 ppm $HCO_3^-$ as $CaCO_3$) was added to an Erlenmeyer flask. An amount of the compound being tested, sufficient to make up 150 ml of solution at the desired concentration, was then added. This was followed by the addition of 75 ml of a $CaCl_2$ solution (2000 ppm $Ca^{+2}$ as $CaCO_3$). The pH of the resulting solution was adjusted to 8.55 with 0.1N NaOH solution. The flask was stoppered and placed in a shaker water bath at 50° C. for 18 hours. A 20 ml aliquot of the solution was removed and filtered through a 0.1 μm membrane while still hot. The filtrate was acidified to pH≈3 with 5% aqueous nitric acid and analyzed for soluble $Ca^{++}$ by inductively coupled plasma spectroscopy. The % scale inhibition was calculated according to the following formula:

$$\% \text{ Scale Inhibition} = \frac{\text{ppm } Ca^{++} \text{ (treated)} - \text{ppm } Ca^{++} \text{ (blank)}}{\text{ppm } Ca^{++} \text{ (initial)} - \text{ppm } Ca^{++} \text{ (blank)}} \times 100$$

As shown in Table 1, the sulfonated organophosphonate compounds of this invention were effective calcium threshold inhibitors.

The following is a list of certain selected sulfonated organophosphonate compounds of this invention that were prepared according to the procedures described herein. Compound numbers were assigned to each compound and were used in the remainder of the application to designate the various compounds being tested.

I) 4-Sulfo-1-aminobutane-1,1-diphosphonic acid.
II) 7-Sulfo-1-aminoheptane-1,1-diphosphonic acid.
III) 5-Sulfo-1-hydroxypentane-1,1-diphosphonic acid.
IV) 6-Sulfo-1-hydroxyhexane-1,1-diphosphonic acid.
V) 8-Sulfo-1-hydroxyoctane-1,1-diphosphonic acid.

TABLE 1

| $CaCO_3$ THRESHOLD INHIBITOR (SHAKER TEST) | | |
|---|---|---|
| COMPOUND | CONC. (ppm) | % INHIBITION |
| I | 0.5 | 0 |

TABLE 1-continued

| $CaCO_3$ THRESHOLD INHIBITOR (SHAKER TEST) | | |
|---|---|---|
| COMPOUND | CONC. (ppm) | % INHIBITION |
| | 1.0 | 63 |
| | 2.0 | 71 |
| | 5.0 | 62 |
| II | 1.0 | 19 |
| | 2.0 | 64 |
| | 2.0 | 71 |
| | 5.0 | 64 |
| III | 1.0 | 5 |
| | 2.0 | 53 |
| | 5.0 | 77 |
| IV | 1.0 | 0 |
| | 2.0 | 48 |
| | 2.0 | 64 |
| | 3.5 | 75 |
| | 5.0 | 81 |
| V | 1.0 | 9 |
| | 2.0 | 22 |
| | 5.0 | 66 |

EXAMPLE 9

The threshold inhibition test measures the ability of a chemical to inhibit calcium carbonate scale formation. The laboratory tests for calcium carbonate threshold inhibitors were performed under the following water conditions: water containing 1000 ppm $Ca^{+2}$ and 328 ppm $HCO_3$ (all as $CaCO_3$). The test solution was prepared in a 1000 ml beaker and 5 ppm of the additive being tested was added to the above water. The final volume of the solution was made up to 800 ml. The solution was stirred with a magnetic stir bar and heated by a stainless steel immersion heater to 120° F. or 130° F. depending on the water condition. The pH of the solution was monitored and adjusted at pH 7.15 with the addition of dilute HCl. On achieving the required temperature, 0.1N NaOH was added at a rate of 0.32 ml/minute using a syringe pump.

The pH was monitored and recorded during the titration. A decrease or plateau in pH reading is observed when calcium carbonate starts to precipitate. This point is termed the critical pH (pHc). An effective threshold inhibitor will raise the critical pH, compared to the blank, and require more base ($OH^-$) to reach pHc. Results are summarized in Table 2.

As shown in Table 2, the sulfonated organophosphonate compounds of this invention were effective calcium carbonate threshold inhibitors.

TABLE 2

| THRESHOLD INHIBITION TEST | | |
|---|---|---|
| Compound | pHc | Meq $OH^-$/liter to pHc |
| BLANK | 7.69 | 0.48 |
| II | 8.49 | 1.04 |
| V | 8.45 | 1.01 |
| HEDPA* | 8.54 | 1.63 |

1000 ppm $Ca^{+2}$, 328 ppm $HCO_3^-$ (as $CaCO_3$); 120° F.
*Hydroxyethylidene Diphosphonic Acid (Comparison Compound).

EXAMPLE 10

Calcium sensitivity test determines the tendency of a chemical to precipitate with calcium ions in solution.

Calcium insensitivity is considered an important feature of this invention because it allows the compound of this invention to be used effectively in water of relatively high hardness. The test for calcium insensitivity of a compound as used in this application involves a cloud point test where the compound is added to a hard water containing 500 ppm calcium ion (as CaCO3) which is buffered at pH 8.3 using 0.005M borate buffer and has a temperature of 60 C. The amount of compound which can be added until the solution becomes turbid (the cloud point) is considered to be an indicator of calcium sensitivity. The calcium insensitive compounds of this invention have cloud points of at least about 25 ppm as determined by this specific test.

Formation of the co-precipitates of calcium with HEDPA, a commercial organophosphonate scale inhibitor, and the sulfonated organophosphonate compounds were at cloud points of 7 ppm and >100 ppm respectively. This result indicates that HEDPA was very sensitive to calcium hardness and prone to form a calcium HEDPA precipitate at low treatment concentrations. In contrast, the sulfonated organophosphonate compounds of this invention, as illustrated in Table 3, were quite insensitive to calcium with no cloud point at all observed under the test conditions (>100 ppm).

TABLE 3
CALCIUM SENSITIVITY TEST

| Compound | Cloud Point (ppm) |
|---|---|
| HEDPA* | 7 |
| IV | >100 |
| V | >100 |

*Hydroxyethylidene Diphosphonic Acid (Comparison Compound)

EXAMPLE 11

The corrosion inhibitor activity of selected sulfonated organophosphonate compounds of this invention was demonstrated by the Aerated Solution Bottle test using a series of standard corrosive waters with the following compositions:

Water A

30 mg/l CaCl2
37 mg/l MgSO4
100 mg/l NASO4
50 mg/l NaCl
100 mg/l Na2CO2

Water B

12.8 mg/l CaCl2
110.7 mg/l CaSO4.2H2O
54.6 mg/l MgSO4
175.7 mg/l NaHCO3

Water C

25.6 mg/l CaCl2
221.4 mg/l CaSO4.2H2O
109.2 mg/l MgSO4
351.4 mg/l NaHCO3

Mild steel coupons (4.5 in. ×0.5 in.) were immersed in 15% hydrochloric acid for 15 minutes, then rinsed sequentially in saturated sodium bicarbonate solution, distilled water and isopropanol, dried and stored in a desiccator. They were weighed prior to use in the corrosion test.

The desired amount of corrosion inhibitor was dissolved in 850 ml of one of the standard corrosive waters listed above. The solution was heated in a thermostatted batch at 55° C. After the temperature had equilibrated, the pH of the solution was adjusted to 8.5. Two coupons were suspended in the solution and air was passed into the solution at 250 ml/min. After 48 hours, the coupons were removed and cleaned with steel wool, rinsed, dried and reweighed. The rate of corrosion was calculated from the weight loss and was expressed in mils per year. The results are shown in Table 3.

TABLE 3
CORROSION INHIBITION - AERATED BOTTLE TEST

| Compound | Dosage (ppm) | CORROSION RATE IN MPY Water A | Water B | Water C |
|---|---|---|---|---|
| BLANK | — | 89 | 75 | 73 |
| I* | 200 | 5.7 | — | — |
|  | 150 | 28 | — | — |
|  | 125 | — | 3.0 | — |
|  | 100 | — | 5.6 | 4.7 |
|  | 75 | — | 49 | 7.8 |
|  | 50 | — | — | 13.0 |
| I** | 100 | — | — | — |
|  | 75 | — | 45 | — |
|  | 50 | — | 60 | 8.1 |
|  | 35 | — | — | 12.0 |
|  | 25 | — | — | 32 |
| III | 200 | 62 | — | — |
|  | 150 | — | 71 | 25 |
|  | 100 | — | — | 35 |
| IV | 250 | 4.7 | — | — |
|  | 200 | 13 | 4.9 | — |
|  | 150 | — | 39 | 13 |
|  | 125 | — | — | 11 |
|  | 100 | — | — | 23 |
| V | 200 | 65 | — | — |
|  | 150 | — | 56 | — |
|  | 100 | — | — | 19 |
|  | 75 | — | — | 17 |

*Prepared in Example 2
**Prepared in Example 3

I claim:

1. A method for inhibiting corrosion of a ferrous based metal in contact with an aqueous system which comprises adding to the aqueous system, in an amount effective to inhibit corrosion, a sulfonated organophosphonate compound having the formula:

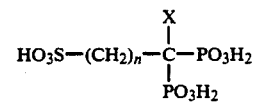

$$HO_3S-(CH_2)_n-\underset{\underset{PO_3H_2}{|}}{\overset{\overset{X}{|}}{C}}-PO_3H_2$$

wherein n is an integer from 3 to 10; X is OH or NH2; and water soluble salts thereof and wherein the sulfonated organophosphonate compound has a cloud point of at least 50 ppm as determined by a CA500 cloud point test.

2. A method according to claim 1 wherein said water soluble salt is an alkali metal salt.

3. A method according to claim 1 wherein said sulfonated organophosphonate compound is added at a concentration of from 0.1 ppm to 10,000 ppm.

4. A method according to claim 1 wherein said sulfonated organophosphonate compound is added at a concentration of from 0.5 ppm to 500 ppm.

5. A method according to claim 1 wherein said sulfonated organophosphonate compound is added at a concentration of from 0.5 ppm to 100 ppm.

6. A method according to claim 1 wherein X is NH2.

7. A method according to claim 6 wherein n is 3.

8. A method according to claim 6 wherein n is 6.

9. A method according to claim 1 wherein X is OH.

10. A method according to claim 9 wherein n is 4.

11. A method according to claim 9 wherein n is 5.

12. A method according to claim 9 wherein n is 7.

* * * * *